United States Patent [19]

Saab

[11] Patent Number: 5,264,260
[45] Date of Patent: Nov. 23, 1993

[54] DILATATION BALLOON FABRICATED FROM LOW MOLECULAR WEIGHT POLYMERS

[76] Inventor: Mark A. Saab, 16 Nesmith St., Lawrence, Mass. 01841

[21] Appl. No.: 717,933

[22] Filed: Jun. 20, 1991

[51] Int. Cl.$^5$ .............................................. A61M 29/02
[52] U.S. Cl. .................................. 428/35.5; 428/35.2; 428/36.92; 428/480; 428/910; 604/96; 606/194; 264/529
[58] Field of Search .................. 604/96, 281, 280; 606/192, 194; 428/36.92, 34.3, 35.2, 480, 910, 35.5; 264/528, 529, 532

[56] References Cited

U.S. PATENT DOCUMENTS

| | | | |
|---|---|---|---|
| Re. 32,983 | 7/1989 | Levy | 428/36.92 |
| Re. 33,561 | 3/1991 | Levy | 428/36.92 |
| 4,130,617 | 12/1978 | Wallace | 264/528 |
| 4,811,737 | 3/1989 | Rydell | 604/96 |
| 4,906,244 | 3/1990 | Pinchuk | 604/96 |
| 4,941,877 | 7/1990 | Montano | 604/96 |
| 4,963,313 | 10/1990 | Noddin | 604/96 |
| 4,986,830 | 1/1991 | Owens | 604/96 |
| 4,998,917 | 3/1991 | Gaiser | 604/96 |
| 4,998,923 | 3/1991 | Samson | 604/96 |
| 5,041,125 | 8/1991 | Montano | 604/96 |

FOREIGN PATENT DOCUMENTS 0274411  1/1987  PCT Int'l Appl. .

OTHER PUBLICATIONS

Levy, Stanley B.; "Improved Dilatation Catheter Balloons"; *Journal of Chemical Engineering;* vol. 11, No. 4, Jul.-Aug. 1986.

*Primary Examiner*—Ellis P. Robinson
*Assistant Examiner*—Rena L. Dye
*Attorney, Agent, or Firm*—Schiller & Kusmer

[57] ABSTRACT

A low molecular weight, flexible, biaxially oriented, dilatation catheter balloon comprising oriented polyethylene terephthalate, and having a calculated radial tensile strength of greater than about 25,000 psi.

22 Claims, No Drawings

DILATATION BALLOON FABRICATED FROM LOW MOLECULAR WEIGHT POLYMERS

This invention relates to polymeric balloons particularly useful on dilatation catheters.

It is now common to use polymeric balloons on catheters for medical dilatation procedures such as percutaneous transluminal coronary angioplasty and other dilatation procedures. Typically, a catheter with a balloon mounted on the distal end thereof is inserted into a body cavity, such as an artery, and inflated. The balloon is usually substantially non-compliant and is typically selected to have a maximum inflated diameter as a function of the inner diameter of the unobstructed and nonstenotic portions of a cavity within which the balloon is to be used. The balloon must be capable, when inflated, of exerting sufficient pressure to permanently dilate stenoses in that cavity, without rupture of the balloon.

A dilatation balloon should preferably possess several desirable properties. It should be thin walled so that it can fold closely around the catheter to a low profile so that the balloon will not cause an obstruction to passage of the catheter through narrow vessels, narrow stenotic passageways and the like; and where, for example, dilatation catheters are used for heart valve dilatations and similar applications, to facilitate percutaneous entry of the catheter into the body as well as entry and withdrawal of the catheter to and from relatively small diameter passageways on the way to and from the heart. The balloon should exhibit high flexibility (exhibit relatively low stiffness) to permit ready folding before inflation and after deflation and to confer trackability on the assembly comprising the catheter and balloon (i.e., the ability of the balloon portion of the dilatation catheter to bend as it is advanced through tortuous passages). Dimensional stability is an important feature so that the balloon can retain its size and structural integrity during storage and, when inflated, will not substantially expand beyond its formed diameter regardless of internal pressures. High burst strength relative to balloon diameter, a function of radial tensile strength, is also quite important, at least in some applications such as balloon angioplasty, to enable the balloon to exert adequate pressure, when inflated, to dilate stenoses without bursting.

In addition to the above, the ideal balloon should have good wall concentricity, bondability, with respect to the catheter, sterilability, non-thrombogenic. See Levy, Stanley B.; "Improved Dilatation Catheter Balloons" *Journal of Chemical Engineering;* Vol. 11, No. 4, July-August, 1986 (hereinafter the "Levy Article").

Balloons made primarily of polyvinyl chloride and polyethylene have been unable to meet one or more of the foregoing criteria. The major drawback is that these materials have relatively low tensile strength. Balloons made primarily of biaxially oriented polyethylene terephthalate (PET), exemplified by the balloons described in U.S. Pat. No. Re. 32,983 issued to S. B. Levy, the Levy Article, and in my European Patent Application published Jul. 13, 1988 as Publication No. 0 274,411 A2, are improvements over the prior art in that, as well-known, the tensile strength of PET increases considerably upon molecular orientation of the polymer. Levy, however insists that it is critical to his product that the intrinsic viscosity of the polymer, a direct function of its molecular weight, be high. He states that the requisite intrinsic viscosity for the starting PET resin has to be 1.0 to 1.3 and equates that range with high molecular weight, and that once extruded, the intrinsic viscosity of the extruded tube and subsequent balloon cannot be below 0.8. Intrinsic viscosities for commercially available starting PET resin range from about 0.55 to 1.04 [dl/gram] so that in order to manufacture balloons in accordance with the teachings of Levy it is important to start with commercially available resins in the upper intrinsic viscosity range of the available materials. Unless otherwise stated, all references herein to measures of intrinsic viscosity shall be considered to be in the units "dl/gram". Similarly, in my European Patent Application, identified-above, the intrinsic viscosity of the starting PET resin used was 1.04, as would be expected in view of the direct comparison made of the data in that Application with the results detailed in the Levy patent.

I have now determined that indeed, dilatation balloons need not at all be limited to high molecular weight PET as taught by Levy and my prior European Application, but surprisingly, when made from a relatively low molecular weight polymer (preferably PET having an intrinsic viscosity of about 0.6 or below) can have thin walls and high radial tensile strengths. Consequently, much thinner balloons can be made with the same burst pressure as that provided by the balloons of Levy. The thinner balloons are more flexible, trackable, and have lower profiles (than the Levy balloons) all with a material which Levy claims can not be used.

A principal object of the present invention is therefore to provide an improved dilatation balloon made of relatively low molecular weight, oriented PET.

The term "polyethylene terephthalate" or PET as used herein is intended to be used in a broad sense in that it generally refers to resins and products thereof in which the major proportion of the polymer is PET. To this end, the PET may be homopolymeric, or a copolymer. For example, the preferred low molecular weight aromatic linear polyester described for making balloons in accordance with the invention is polyethylene terephthalate derived from an aromatic dicarboxylic acid or its derivatives as a main acid component and an aliphatic glycol as a main glycol component. This polyester is a melt extrudable orientable semicrystalline polymer. Typical examples of other aromatic dicarboxylic acid polymers that meet these criteria utilize materials such as terepthalic acid, isothalic acid, napthalene dicarboxylic acid, together with aliphatic polymethylene glycols having two to ten carbon atoms. Among these are ethylene glycol, trimethylene glycol, tetramethylene glycol, pentamethylene glycol, hexamethylene glycol, didecamethylene glycol and cyclohexane dimethanol. In addition to homopolymers and copolymers, other polymers or non polymeric materials may be melt blended or mixed together. These materials can be used to modify or alter final balloon properties, for example, surface roughness, radial expansion vs pressure characteristics, adhesion, flexibility, etc. However, these variations do not substantially affect the basic properties of PET, namely orientability and high tensile strength derived from the orientation process.

Accordingly, the flexible dilatation catheter balloon of the present invention can be formed (for example, by extrusion) into a tubular parison of orientable polymer from a starting resin of relatively low molecular weight material, a starting resin of PET having an intrinsic viscosity of about 0.6 or below being preferred. The parison preferably is stretched close to the elastic limit of the material by axially stretching and radially expanding the balloon to provide the desired orientation. The balloon can then be heat set to increase the crystallinity and improve the dimensional stability of the material. In this manner, one can obtain a balloon having a radial tensile strength of greater than about 25,000 psi, and preferably greater than about 35,000 psi, notwithstanding that the balloon has an intrinsic viscosity of less than or equal to about 0.6. In this regard, it should be appreciated that the intrinsic viscosity of the starting resin can be greater than 0.6 so long as the intrinsic viscosity of the finished balloon material is less than or equal to about 0.6.

It should be noted that although burst pressure is an important characteristic of the product, tensile strength is a more important aspect. The tensile strength in the hoop or radial direction can be calculated using the following equation:

$$T_s = \frac{PD}{2t}$$

where:

$T_s$ is the tensile or hoop stress;
P is the pressure;
D is the diameter of the balloon; and
t is the wall thickness.

If the burst pressure is used for P, then the radial tensile strength can be readily calculated from this equation.

The process and apparatus used to form the balloons from the polymer is substantially as described in my European Patent Application, identified above, the same being incorporated herein by reference. Basically, the process comprises the steps of axially drawing and radially expanding a parison or piece of tubing of a polymer that differs from that detailed in the European Patent Application in that the extruded polymer employed in the present invention has an intrinsic viscosity of about 0.6 or below. Orientation occurs at a temperature between the first and second order transitions of the polymer. Preferably, the tube is drawn axially and before, during or after the axial stretching, the tubing is also expanded radially by introduction of a pressurized fluid internally into the tubing. It should be understood that simply introducing the pressurized fluid for radial expansion will result in axial orientation as well. However, it is preferred to include separate means for controlling axial orientation especially in the conical ends and necks of the balloon. The biaxially oriented balloon can then be heat set (at a temperature above the forming temperature and below the melting temperature) to increase the crystallinity thereof. The expanded and drawn tubing is then cooled to less than the second order transition temperature. Heat setting generally increases crystallinity and dimensional stability. Heat setting can also be used to stress relieve the balloon. Thus, heat setting can be used in various ways to both stabilize the balloon and also to modify the stress strain curve or the radial expansion as a function of pressure. The details of the preferred temperature, pressure, stretch ratios and the like, are provided in the above-identified European Application.

Several balloons were prepared according to the principles of the present invention, the specifications and results being set forth in Table A appearing hereinafter. In Table A, the first column (Tube ID) describes the inner diameter of the starting parison in inches, and the second column (Tube OD) sets forth the outer diameter of that parison (also in inches). The next two columns (IDS and ODS) provide respectively the stretch ratios i.e. the ratio of the inner diameter of the balloon to the inner diameter of the original parison, and the ratio of the outer diameter of the balloon to the outer diameter of the original parison. The fifth column (DIAM) sets forth the balloon diameter in inches measured at 75 psi. The sixth column (THICK) describes the wall thickness of the finished balloon, and the seventh column (BURST) provides the burst pressure in psi for the balloon. The last column (TENSILE) sets forth the radial tensile strength in psi, calculated as above-described.

TABLE A

| Tube ID | Tube OD | IDS | ODS | DIAM. | THICK | BURST | TENSILE |
|---|---|---|---|---|---|---|---|
| 0.0158 | 0.0261 | 7.3 | 4.4 | 0.116 | 0.000235 | 211 | 52,000 |
| 0.012 | 0.0198 | 6.36 | 3.8 | 0.075 | 0.000265 | 265 | 37,500 |
| 0.0128 | 0.021 | 6.5 | 4.0 | 0.0835 | 0.0002 | 235 | 49,000 |
| 0.0074 | 0.0167 | 7.6 | 3.4 | 0.056 | 0.000265 | >400 | >42,000 |
| 0.0118 | 0.0209 | 8.2 | 4.6 | 0.097 | 0.0002 | 239 | 58,000 |
| 0.0098 | 0.0257 | 9.9 | 3.8 | 0.097 | 0.0003 | 309 | 50,000 |

In each case set forth in Table A, the parisons were made from a sample of a starting PET resin (sold as "TRAYTUF 5900C" by The Goodyear Tire & Rubber Company of Apple Grove, W.V. with a specified intrinsic viscosity of 0.59 by the manufacturer) having a measured intrinsic viscosity of 0.568. Measurements made of the resulting products established that all of the balloons had intrinsic viscosities of between 0.53 and 0.54. Table B summarizes the samples:

TABLE B

| Samples | I.V. Value (dl/gram) |
|---|---|
| Specified Resin Value | 0.59 +/− 0.02 |
| Measured Resin Value | 0.568 |
| Measured Value of extruded tubing/balloons | 0.053–0.054 |

As seen from the data in TABLE A, these balloons were thinner and have higher tensile strengths than achieved by Levy.

It should be appreciated that all of the specific values of intrinsic viscosity given herein have been determined using guidelines specified in the ANSI/ASTM D 2857-70 standard mentioned in Levy reissue patent, identified above.

Certain changes may be made in the above product without departing from the scope of the invention herein involved. It is therefore intended that all matter contained in the above description shall be interpreted in an illustrative and not in a limiting sense.

What is claimed is:

1. A thin-walled, flexible, dilation catheter balloon having an intrinsic viscosity less than or equal to 0.6 dl/gram and a calculated radial tensile strength greater than about 25,000 psi, and consisting essentially of oriented polyethylene terephthalate.

2. A balloon as set forth in claim 1, wherein said polyethylene terephthalate is a copolymer.

3. A balloon as set forth in claim 1, wherein said polyethylene terephthalate is biaxially oriented.

4. A flexible, oriented, dilation catheter balloon having an intrinsic viscosity of not more than about 0.6 dl/gram and a calculated radial tensile strength greater than about 25,000 psi, and consisting essentially of oriented polyethylene terephthalate.

5. A balloon as set forth in claim 4, wherein said polyethylene terephthalate is a copolymer.

6. A balloon as set forth in claim 4, wherein said polyethylene terephthalate is biaxially oriented.

7. A balloon as set forth in claim 4, wherein the calculated radial tensile strength is greater than about 35,000 psi.

8. A flexible, oriented, dilatation catheter balloon having an intrinsic viscosity of less than about 0.6 dl/gram and a calculated radial tensile strength greater than about 25,000 psi, and consisting essentially of oriented polyethylene terephthalate.

9. A balloon as set forth in claim 8, wherein said polyethylene terephthalate is a copolymer.

10. A balloon as set forth in claim 8, wherein said polyethylene terephthalate is biaxially oriented.

11. A balloon as set forth in claim 8, wherein the calculated radial tensile strength is greater than about 35,000 psi.

12. Medical apparatus for use as or in combination with a balloon dilatation catheter, said apparatus comprising a very thin-walled, flexible, high strength balloon having an intrinsic viscosity equal to or less than about 0.6 dl/gram and a calculated radial tensile strength greater than or equal to 25,000 psi, and consisting essentially oriented polyethylene terephthalate.

13. Medical apparatus according to claim 12 wherein said polyethylene terephthalate is biaxially oriented.

14. Medical apparatus according to claim 12 wherein said balloon has a wall thickness equal to or less than about 0.0003 inches.

15. Medical apparatus according to claim 12 further wherein said balloon has a radial tensile strength equal to or greater than about 35,000 psi.

16. Medical apparatus according to claim 12 wherein said polyethylene terephthalate is a copolymer.

17. Medical apparatus for use as or in combination with a balloon dilatation catheter made by the method of axially drawing and radially expanding a tubular section of low molecular weight polyethylene terephthalate so as to expand and orient the polymer in two directions to form a balloon having an intrinsic viscosity equal to or less than about 0.6 dl/gram and a calculated radial tensile strength greater than or equal to 25,000 psi.

18. Medical apparatus according to claim 17 wherein said tubular section consists essentially of polyethylene terephthalate having an intrinsic viscosity of about 0.6 dl/gram or below.

19. Medical apparatus according to claim 17 wherein said tubular section is stretched axially and, before, during or after the axial stretching, is expanded radially by introduction of a pressurized fluid internally into said tubular section.

20. Medical apparatus according to claim 17 wherein said balloon has a wall thickness equal to or less than about 0.0003 inches.

21. Medical apparatus according to claim 17 wherein said balloon has a radial tensile strength equal to or greater than about 35,000 psi.

22. Medical apparatus according to claim 17 wherein said polyethylene terephthalate is a copolymer.

* * * * *